US007625358B2

(12) United States Patent  (10) Patent No.: US 7,625,358 B2
Mernoe  (45) Date of Patent: Dec. 1, 2009

(54) FLEXIBLE PISTON ROD

(75) Inventor: Morten Mernoe, Charlottenlund (DK)

(73) Assignee: M2 Group Holdings, Inc., Sunnyvale, CA (US)

( * ) Notice: Subject to any disclaimer, the term of this patent is extended or adjusted under 35 U.S.C. 154(b) by 66 days.

(21) Appl. No.: 11/697,168

(22) Filed: Apr. 5, 2007

(65) Prior Publication Data
US 2007/0203459 A1  Aug. 30, 2007

Related U.S. Application Data

(63) Continuation of application No. 11/158,277, filed on Jun. 21, 2005, now Pat. No. 7,220,248, which is a continuation of application No. PCT/DK03/00915, filed on Dec. 19, 2003.

(30) Foreign Application Priority Data
Dec. 23, 2002 (DK) ............................. 2002 02007

(51) Int. Cl.
*A61M 5/315* (2006.01)
(52) U.S. Cl. ................ 604/224; 604/155; 604/218
(58) Field of Classification Search .......... 604/131, 604/134, 135, 154, 155, 187, 207–210, 218, 604/223, 224, 228
See application file for complete search history.

(56) References Cited

U.S. PATENT DOCUMENTS

| 4,265,241 | A | 5/1981 | Portner et al. |
| 5,250,027 | A | 10/1993 | Lewis et al. |
| 6,171,276 | B1 | 1/2001 | Lippe et al. |
| 7,128,727 | B2 | 10/2006 | Flaherty et al. |
| 7,232,423 | B2 | 6/2007 | Mernoe |
| 2002/0126036 | A1 | 9/2002 | Flaherty et al. |
| 2003/0065308 | A1 | 4/2003 | Lebel et al. |
| 2004/0171983 | A1 | 9/2004 | Sparks et al. |
| 2005/0267402 | A1 | 12/2005 | Stewart et al. |
| 2007/0073228 | A1 | 3/2007 | Mernoe et al. |
| 2007/0073236 | A1 | 3/2007 | Mernoe et al. |
| 2007/0124002 | A1 | 5/2007 | Estes et al. |
| 2007/0156092 | A1 | 7/2007 | Estes et al. |
| 2007/0167905 | A1 | 7/2007 | Estes et al. |
| 2007/0167912 | A1 | 7/2007 | Causey et al. |
| 2007/0276329 | A1* | 11/2007 | Mernoe ...................... 604/155 |

OTHER PUBLICATIONS

Japanese Patent Office, Office Action Application No. JP 2004-561090 mailed Jul. 23, 2009, with English translation 5 pages.

* cited by examiner

*Primary Examiner*—Kevin C Sirmons
*Assistant Examiner*—Bhisma Mehta
(74) *Attorney, Agent, or Firm*—Fish & Richardson P.C.

(57) ABSTRACT

A flexible piston rod includes a piston and a row of elements, the top surface of one element being connected to the bottom surface of an adjacent element by a hinge that allows the two adjacent elements to pivot from a first position, where a portion of the top surface of one element abuts a corresponding portion of the bottom surface of the adjacent element and corresponding to a rectilinear, relatively stiff configuration of the piston rod, to a second position wherein the top surface of one element is spaced from the bottom surface of the adjacent element and corresponding to a curved configuration of the piston rod. Each element has cylindrical surface portions incorporating a thread for meshing with a corresponding thread of an actuator for displacing the piston rod longitudinally.

16 Claims, 5 Drawing Sheets

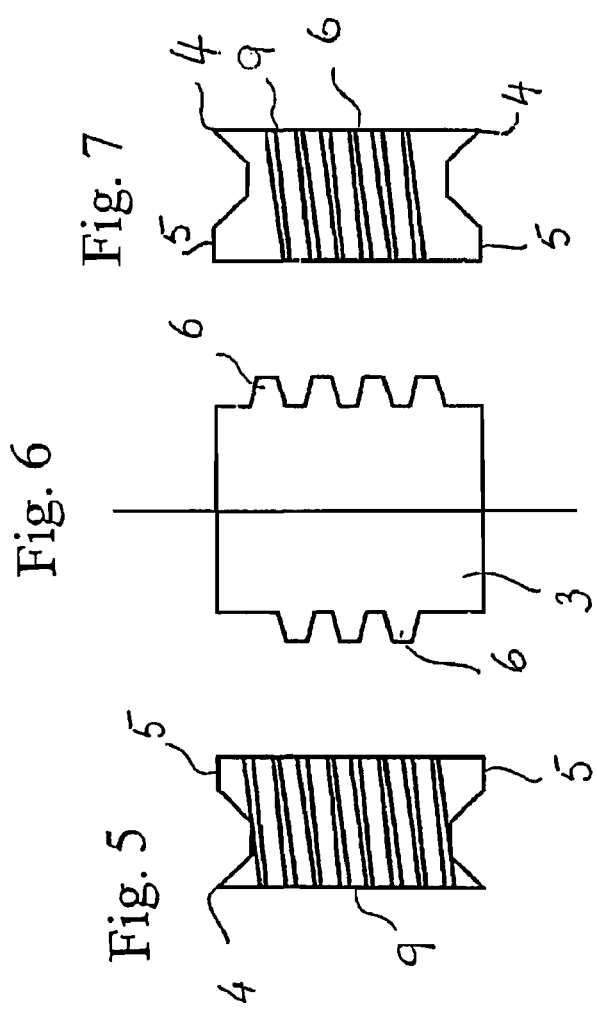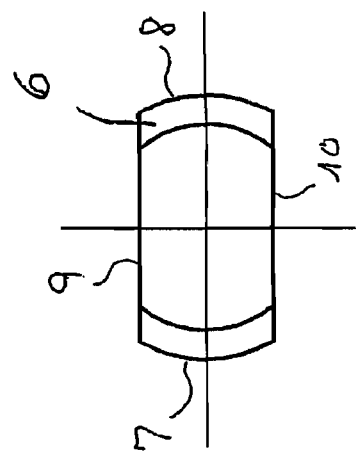

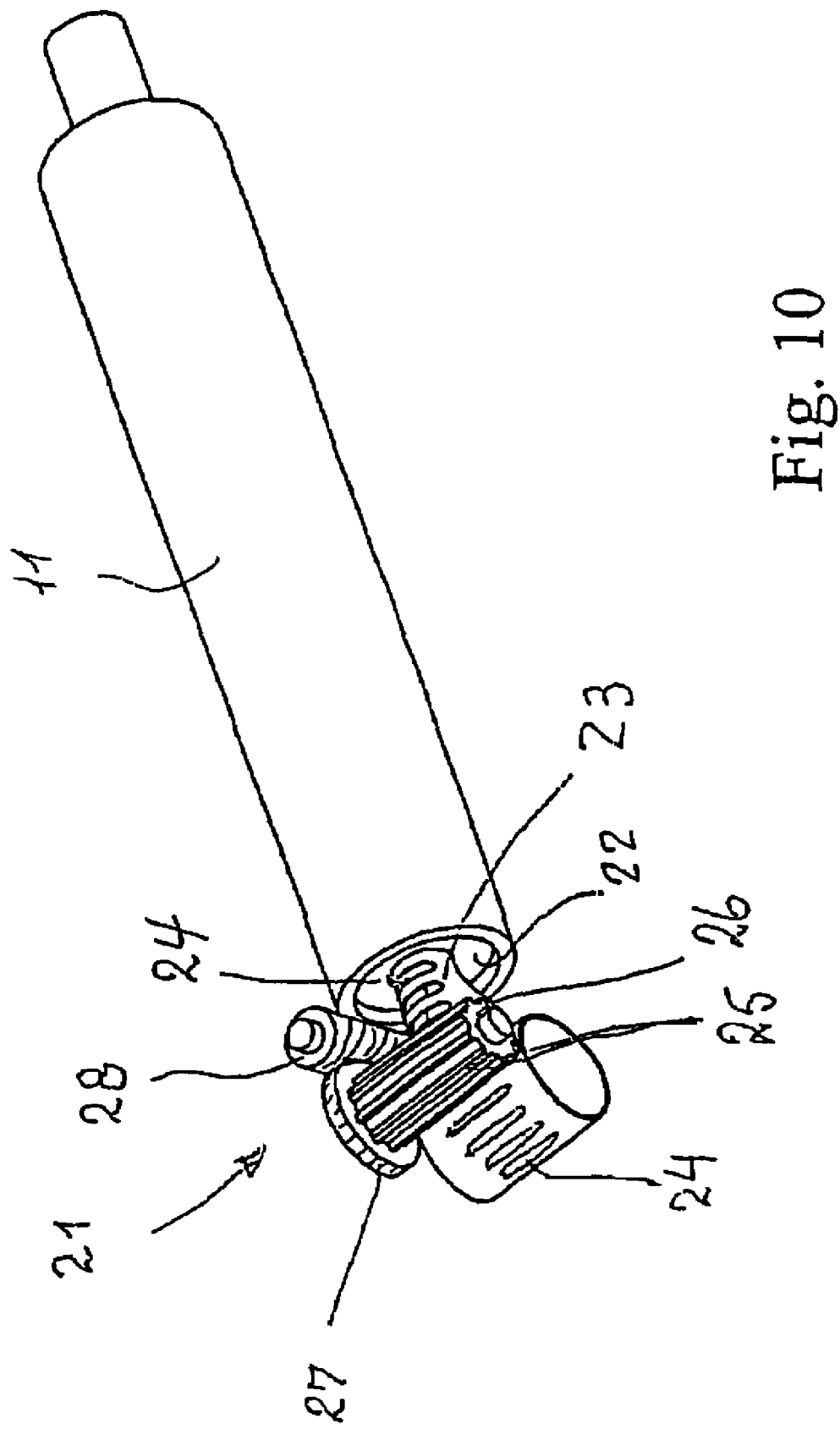

FLEXIBLE PISTON ROD

CROSS-REFERENCE TO RELATED APPLICATIONS

This application is a continuation of U.S. patent application Ser. No. 11/158,277 now U.S. Pat. No. 7,220,248, filed on Jun. 21, 2005 by Morten Mernoe, which is a continuation of PCT Application No. PCT/DK2003/000915 filed Dec. 19, 2003 by Morten Mernoe, which claims priority to Denmark Application No. PA200202007 filed on Dec. 23, 2002 by Morten Mernoe. The disclosures of these previous applications are incorporated herein by reference.

FEDERALLY SPONSORED RESEARCH OR DEVELOPMENT

Not Applicable

BACKGROUND

The present invention relates to a flexible piston rod, particularly for use in medicine dispensing devices.

So as to render devices and applications where a piston rod is to linearly displace an object more compact it is desirable to avoid the space requirements necessary for allowing a rigid rectilinear piston rod to travel the entire displacement length along its axis. Several flexible piston rods have been conceived embodying a coil spring supported by an internal curved mandrel or guide rod or various elements collaborating with one another. All the known flexible piston rods are either too complicated or require relatively large forces to be displaced.

SUMMARY

An object of the present invention is to provide a flexible piston rod that is simple to manufacture and operate and requires relatively small displacement forces.

According to the invention this object is achieved by the piston rod comprising a row of elements each having a top surface and a bottom surface as well as a lateral surface, the top surface of one element being connected to the bottom surface of the adjacent element by a hinge means located and adapted to allow the two adjacent elements to pivot from a first position where at least a portion of a top surface of one element abuts a corresponding portion of the bottom surface of the adjacent element, said first position corresponding to a rectilinear, relatively stiff configuration of the piston rod, to a second position wherein said top surface of one element is spaced from said bottom surface of the adjacent element corresponding to a curved configuration of said flexible piston rod.

In the currently preferred embodiment of a flexible piston rod according to the invention, said lateral surface has first and a second mutually opposed circular cylindrical surface portions incorporating a screw thread for meshing with a corresponding screw thread of an actuator for displacing the piston rod in the longitudinal direction thereof. Hereby a simple displacement mechanism which is self supporting and self centering is achieved.

Preferably, at least one surface portion disposed between said first and second surface portion is a plane so as to allow co-operation with means to prevent rotation of the piston rod around the longitudinal axis thereof when said screw threads on the lateral surface of said elements are engaged by said actuator screw threads.

Preferably, said portions of said top and bottom surfaces are spaced from said hinge. Hereby a particularly stable rectilinear configuration of the piston rod is achieved.

Advantageously, said elements and said hinges form an integrally molded piston rod molded in one piece from a moldable material, preferably a plastic material such as Nylon or POM.

In another aspect, the present invention relates to a flexible piston rod comprising a strip of relatively stiff and resilient material such as steel having in the relaxed state an arcuate cross section taken transversely to the longitudinal direction of said strip, a longitudinal row of evenly space apertures being provided along the length of said strip for receiving projection of an actuator for displacing said strip in the longitudinal direction thereof, and preferably the major portion of the said strip is rolled into a roll when the piston rod is in its least extended condition.

In the following, the invention will be described and explained more in detail with reference to embodiments thereof shown, solely by way of example, in the accompanying drawings, where

BRIEF DESCRIPTION OF THE DRAWINGS

FIG. 10 is a schematic isometric view of second embodiment of a flexible piston rod applied to a medicine dispensing device.

DETAILED DESCRIPTION

Figure 1:
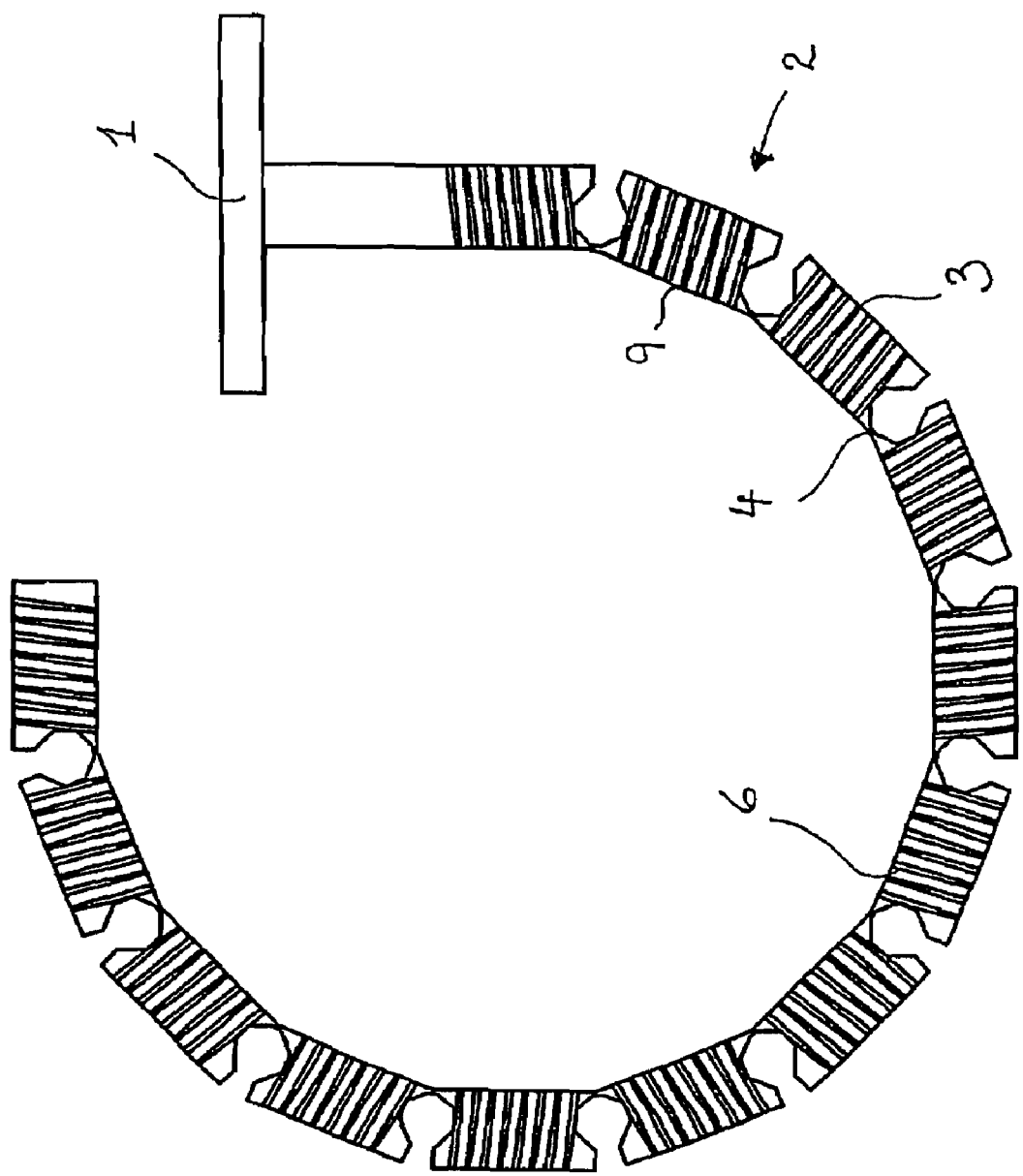
FIG. 1 is a schematic view of a first embodiment of a flexible piston rod according to the invention.
Figure 4:
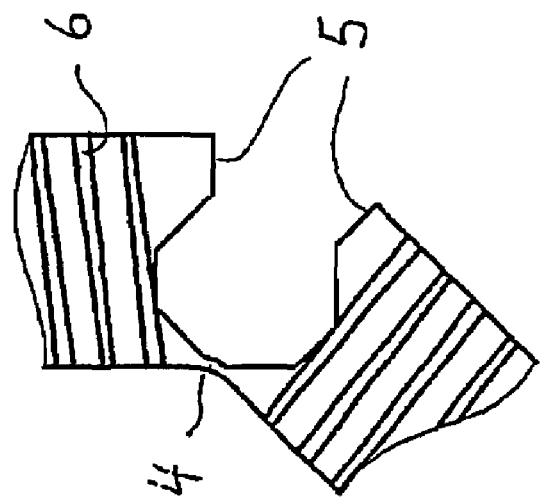
FIGS. 2-4 are schematic enlarged scale views of the hinge mechanism of the flexible piston rod according to FIG. 1, FIGS. 5-8 are schematic enlarged scale views from different angles of an element of the flexible piston rod of FIG. 1.
Figure 3:
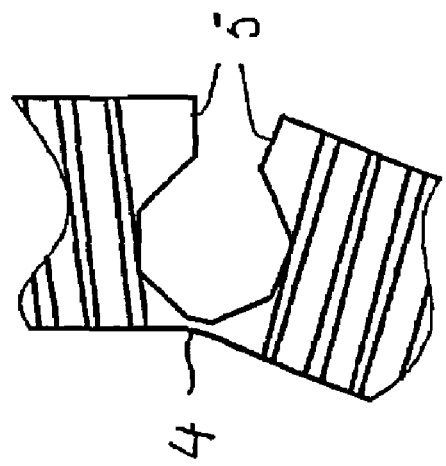
Figure 2:
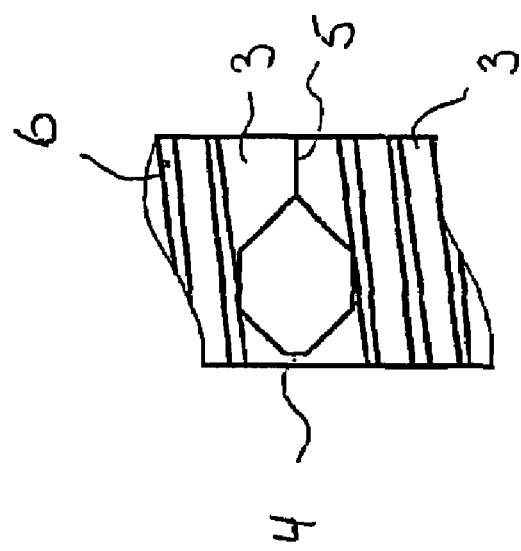

Referring now to FIGS. 1-8, a piston 1 is attached to one end of a flexible piston rod 2 constituted by a series of elements 3 interconnected by hinges 4. The elements 3 are integral with each other by means of the hinges 4 which allow mutually adjacent elements to pivot relative to one another from the position abutting one another shown in FIG. 2 wherein the elements 3 together form a rectilinear piston rod with abutment surfaces 5 and hinges 4 affording rigidity and thus rendering the piston rod 2 capable of exerting a pressure on the piston 1 without deflecting laterally, to the position shown in FIG. 4 wherein the elements 3 are pivoted way from one another so as to allow the curvature of the piston rod 2.

Figure 9:
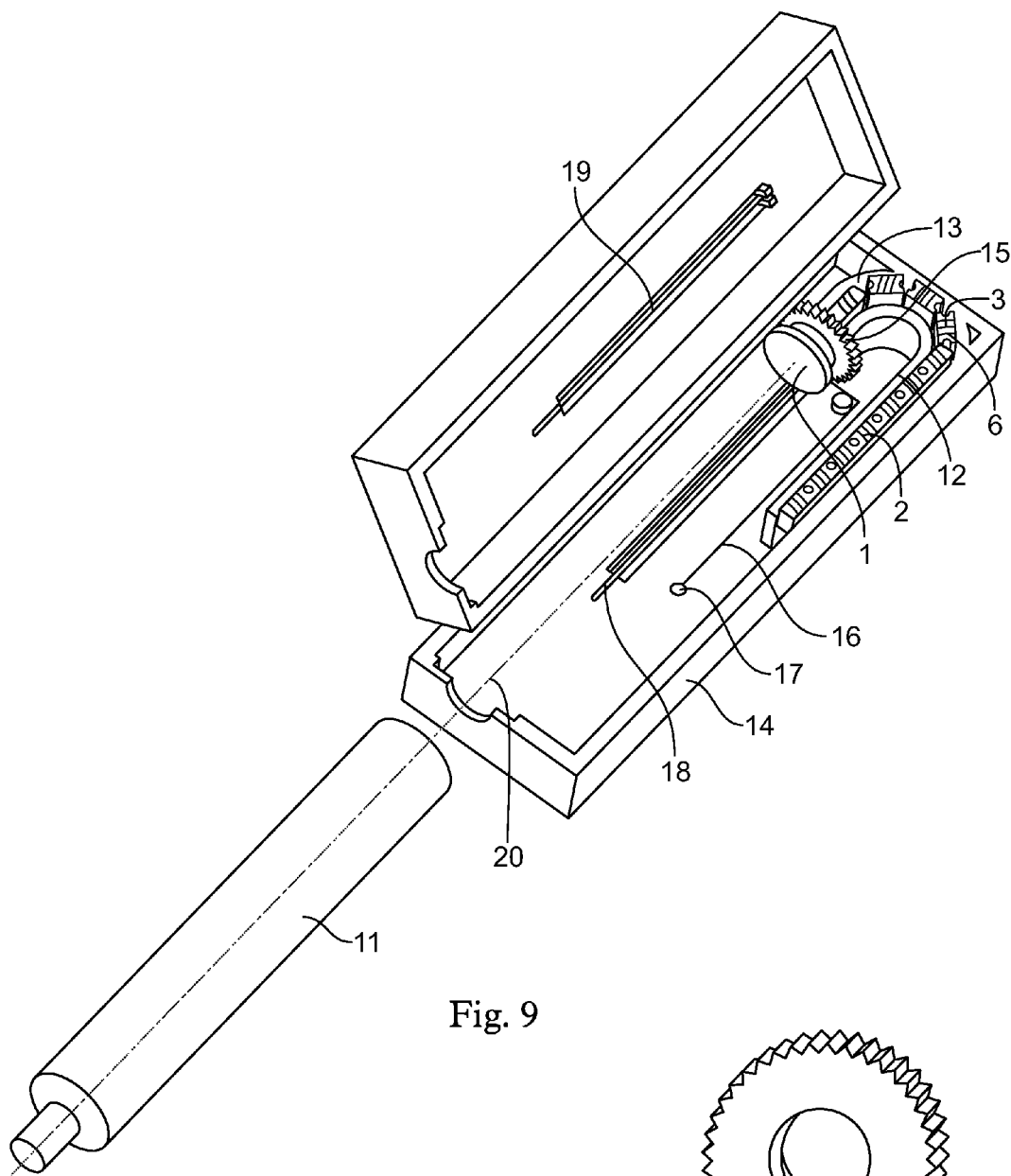
FIG. 9 is a schematic isometric view of a medicine dispensing device incorporating a flexible piston rod as shown in FIG. 1.

This ability to curve allows the compact configuration of any device utilizing the flexible piston rod 2 to linearly displace an object because the initially major part of the piston rod may extend along the intended path of travel of the piston 1 during such displacement of said object, see FIG. 9 and the corresponding explanation.

The material of the flexible piston rod 2 may any suitable moldable material, but it is preferred that it be a plastic material such as Nylon or POM. The elements, hinges and piston are molded in one piece in a single molding operation which reduces the manufacturing cost considerably.

Each element 3 is provided with exterior threads 6 on two opposed portions 7 and 8 of the elements having a circular cylindrical configuration. At least the side 9 of the elements 3 coinciding with the hinges 4 is flat to allow practical molding of the hinge. A further function of the flat side 9 or preferably two opposed flat sides 9 and 10 is to allow preventing rotation of the piston rod 2 around its axis when being axially displaced by the threads of an actuator meshing with the threads 6; see for instance FIG. 9.

Referring now to FIG. 9, the flexible piston rod 2 is shown in use for dispensing insulin from a carpule 11 shown before being placed in operational position for greater clarity and having a not shown internal piston for being abutted and displaced by the piston 1. The piston rod 2 is arranged for movement between two guide walls 12 and 13 in a housing 14 of the device. The piston 1 abuts the not shown displaceable wall or piston of the carpule 11 such that axial displacement of the piston 1 will press insulin out of the carpule 11 into a not shown needle for injection into a patient.

Figure 9A:
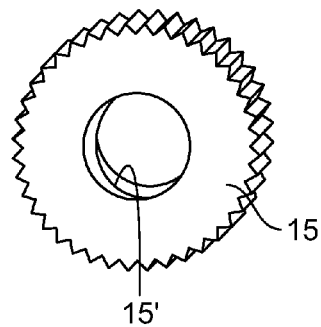
FIG. 9a is a perspective view of an element of the medicine dispensing device shown in FIG. 9.

A gear 15 mounted for rotation in the housing 14 is provided with a central aperture through which the elements 3 of the piston extend. The internal aperture is provided with a screw thread meshing 15' (refer to FIG. 9a) with the screw thread 6 of the piston elements 3 such that rotation of the gear 15 entails displacement of the piston 1 into the carpule 11.

The gear 15 is rotated by a shape memory alloy actuator comprising a wire 16 of a shape memory alloy such as Nitinol, one end of which is attached to a rivet 17 and the other end of which is attached to the free end of an actuator spring rod 18.

The free end of the actuator spring rod 18 is located such that it meshes with the teeth of the gear 15 and is biased by the spring force of the rod to exert a spring force in the tangential direction and in the radial direction.

A pawl spring rod 19 is located such that the end thereof meshes with the teeth of the gear 15 and is biased to exert a spring force in the radial direction. This end of the pawl spring rod 19 is constrained to substantially only move in the radial direction by two not shown stop pins.

A not shown battery supplies power to the ends of the nitinol wire 16 for heating it so as to cause it to contract.

Rotation of the gear 15 is brought about by alternatingly heating and cooling the nitinol wire 16 so that it contracts and cocks the spring rod 18 while the pawl spring rod holds the gear 15 against rotation and thereafter expands and allows the spring rod to turn the gear and advance the piston rod 2.

The flat surfaces 9 and 10 of the elements 3 abut the flat surfaces of the guide walls 12 and 13 and prevent the piston rod 2 from rotating around the longitudinal axis 20 thereof under the influence of the rotating gear 15.

The flexible piston rod 2 could also be displaced by means of another actuator, for instance a worm gear:

Referring now to FIG. 10, a carpule 11 identical to the one described in connection with FIG. 9 is located adjacent an actuator generally referenced by the numeral 21 with a piston 22 of the actuator abutting the not visible piston of the carpule.

The piston 22 is attached to the end of a steel strip 23 having an arcuate cross section taken at right angles to the longitudinal direction of the strip 23. This arcuate shape entails a rigidity of the strip 23 against lateral deflection such that the strip can transmit pressure forces to the piston 22 without collapsing because of lateral deflection.

A row of evenly spaced elongate apertures 24 are provided in the strip 23 for receiving ribs 25 of a roller 26 having a gear 27 meshing with a worm gear 28. The worm gear is actuated by an actuator that may be similar to the shape memory alloy actuator of FIG. 9.

By rotating the worm gear 28 the gear 27 and roller 26 are rotated whereby the ribs 25 received in the apertures 24 unwind the strip 23 from the roll and displace it into the carpule 11 whereby the piston 22 displaces the carpule piston and dispenses the insulin from the carpule 11 that is located in the dispensing device in the same manner as the carpule 11 of FIG. 9.

The invention claimed is:

1. An infusion pump device for dispensing medication, comprising:
   a pump housing defining a cavity to receive a medicine;
   a flexible push rod disposed in the pump housing to longitudinally advance into the cavity, the push rod comprising a plurality of rod segments hingedly connected in serial so that at least a portion of the flexible push rod is adjustable from a curved shape to a noncurved shape, each rod segment including an exterior thread pattern along at least one generally cylindrical surface portion; and
   a rotatable element mounted for rotation in the housing and having an interior screw thread to mate with the exterior thread pattern of the flexible push rod, wherein the rotatable element advances the flexible push rod into the cavity to cause dispensation of the medicine when the medicine is received in the cavity.

2. The pump device of claim 1, wherein when a portion of the flexible push rod is adjusted to the noncurved shape, that portion of the push rod is in a rectilinear, relatively stiff configuration.

3. The pump device of claim 2, wherein the rod segments in the portion of the push rod in the noncurved shape each have a top surface that abuts a bottom surface of an adjacent rod segment.

4. The pump device of claim 1, wherein when a portion of the flexible push rod is adjusted to the curved shape, the rod segments in that portion of the flexible push rod are pivoted away from one another.

5. The pump device of claim 1, further comprising an actuator that is activated to incrementally rotate the rotatable element.

6. The pump device of claim 5, wherein the actuator comprises a shape memory alloy wire.

7. The pump device of claim 1, wherein the cavity of the pump housing is sized to receive a medicine cartridge containing the medicine for displacement of the push rod into the medicine cartridge.

8. The pump device of claim 1, wherein the medicine is insulin.

9. The pump device of claim 1, wherein the rod segments extend serially in a longitudinal direction, and the at least one generally cylindrical surface portion of each rod segment extends axially in the longitudinal direction.

10. The pump device of claim 1, wherein each rod segment includes at least one flat side to impede rotation of the flexible push rod when the rotatable element advances the flexible push rod into the cavity.

11. The pump device of claim 10, wherein each rod segment includes two opposing flat sides to impede rotation of the flexible push rod when the rotatable element advances the flexible push rod into the cavity.

12. The pump device of claim 11, wherein each rod segment includes two generally cylindrical surface portions along which the exterior thread pattern is exposed.

13. The pump device of claim 1, wherein the flexible push rod is integrally molded in one piece from a moldable plastic material.

14. The pump device of claim 13, wherein the moldable plastic material comprises a material selected from the group consisting of Nylon or POM.

15. The pump device of claim 1, wherein the plurality of rod segments are serially connected by hinge structures, each hinge structure comprising an integrally formed, flexible material extending in a direction generally away from a top surface of the one rod segment and generally toward a bottom surface of the adjacent rod segment.

16. The pump device of claim 1, wherein the exterior thread pattern is a discontinuous thread pattern.

* * * * *